United States Patent [19]
Dietert

[11] 3,967,722

[45] July 6, 1976

[54] SAMPLE FEED AUGER STRUCTURE

[75] Inventor: Harry W. Dietert, Kerrville, Tex.

[73] Assignee: Harry W. Dietert Co., Detroit, Mich.

[22] Filed: May 6, 1974

[21] Appl. No.: 467,152

Related U.S. Application Data

[62] Division of Ser. No. 260,985, June 8, 1972, Pat. No. 3,808,881.

[52] U.S. Cl. .............................. 198/213; 222/413
[51] Int. Cl.² ................................. B65G 33/00
[58] Field of Search ............. 198/213, 64, 214–217; 259/191; 222/412, 413

[56] References Cited
UNITED STATES PATENTS

| | | | |
|---|---|---|---|
| 2,888,128 | 5/1959 | Allen | 198/64 |
| 3,360,108 | 12/1967 | Voss | 198/213 |
| 3,705,644 | 12/1972 | Kawchitch | 198/213 |
| 3,709,357 | 1/1973 | Brown | 198/213 |
| 3,727,746 | 4/1973 | Slusher | 198/213 |

Primary Examiner—Robert J. Spar
Assistant Examiner—James M. Slattery
Attorney, Agent, or Firm—Whittemore, Hulbert & Belknap

[57] ABSTRACT

Granular material sample feed structure including a feed auger comprising an elongated rigid hollow cylinder having annular, exterior, axially spaced apart recesses, a plastic sleeve secured on the cylinder as by molding having annular interior portions spaced apart longitudinally thereof within the recesses in the cylinder whereby the plastic sleeve is locked onto the rigid cylinder again axial movement with respect thereto, a flexible, helical auger fin integral with the plastic sleeve progressing axially of the rigid cylinder and tapered toward the outer periphery of the fin, and a rigid trough closely surrounding a portion of the rigid cylinder, plastic sleeve and auger fin over approximately 180 degrees of the auger fin, and a device for rotating the cylinder, plastic sleeve and auger fin connected to the rigid cylinder.

1 Claim, 2 Drawing Figures

SAMPLE FEED AUGER STRUCTURE

This is a division of application Ser. No. 260,985, filed June 8, 1972, now U.S. Pat. No. 3,808,881.

BACKGROUND OF THE INVENTION

1. Field of the Invention

The invention relates to sample feed structure and refers more particularly to a feed auger including a tapered, helical, flexible fin thereon.

2. Description of the Prior Art

In the past, feed augers have generally included rigid, helical fins which have been untapered over their entire radius. Wherein the feed augers of the past have been in conjunction with the rigid troughs, they have been damaged by large, hard articles placed in the trough. Further, feed augers of the past have not generally been contructed of a plastic sleeve with a flexible fin thereon molded over a rigid cylindrical member having spaced apart, annular, external recesses therein for rotation therewith without relative axial movement therebetween.

SUMMARY OF THE INVENTION

In accordance with the present invention, there is provided sample feed structure including a feed auger comprising a rigid, hollow metal member having annular, exterior recesses therein, a urethane plastic sleeve molded on the hollow cylindrical member whereby the sleeve is prevented from relative axial movement with respect to the rigid cylinder and is secured to the rigid cylinder for rotation therewith, which sleeve includes a flexible, helical fin integral therewith which is tapered toward the outer periphery of the fin in conjunction with a rigid trough extending over substantially 180° of the feed auger structure and in closely spaced relation thereto. Means for rotating the feed auger are provided.

Figure 1:
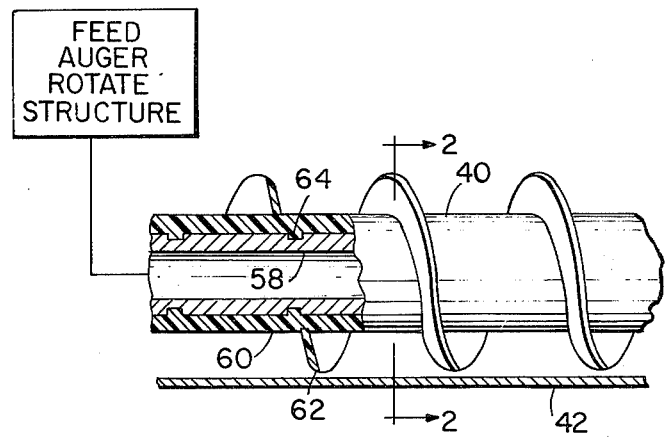
FIG. 1 is a partly broken away, longitudinal elevation view of the sample feed structure of the invention, showing the trough in section in conjunction with the feed auger.
Figure 2:
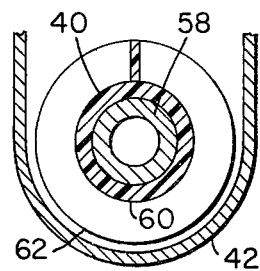
FIG. 2 is a cross section of the sample feed structure illustrated in FIG. 1, taken substantially on the line 2—2 in FIG. 1.

The sample feeder 18 includes a feed auger 40, best shown in FIG. 1, which is rotatably supported in a feed trough 42.

The feed auger 40, as shown best in FIG. 1, includes a metal cylinder 58, adapted to be rotated by conventional means such as a gear (not shown) secured to one end thereof. A plastic sleeve 60 with integral helical auger fins 62 thereon is molded on the cylinder 58. The fins are flexible urethane and as shown are tapered toward the outer periphery thereof. The annular recesses 64 in the cylinder 58 lock the plastic sleeve 60 onto the cylinder 58 against axial movement with respect thereto.

In operation, material such as foundry sand is moved through the trough 42 on rotation of the feed auger 40, and should hard, foreign objects such as nails, bolts or the like be fed into the sample feeder 18, they will be passed through the trough 42 without damage to the feed auger 40 or trough 42 due to deformation of the outer periphery of the fins 62 in contact with the hard objects. Thus, no shutdown time is required with the sample feeder 18 due to broken shear pins or actuation of overload relays due to hard objects jammed between the feed auger and trough.

While one embodiment of the present invention has been considered in detail herein, it will be understood that other embodiments and modifications thereof are contemplated by the inventor. It is, therefore, intended to include all embodiments and modifications as are defined by the appended claims within the scope of the invention.

What I claim as my invention is:

1. Sample feed structure comprising feed auger structure including an elongated, rigid, hollow cylinder, annular, exterior, axially spaced apart recesses in the exterior surface of the rigid cylinder, a plastic sleeve secured on the cylinder for rotation therewith having annular interior portions spaced apart longitudinally thereof extending within the recesses in the cylinder for locking the plastic sleeve on the rigid cylinder against axial movement with respect thereto, and a flexible helical auger fin integral with the plastic sleeve progressing axially of the rigid cylinder and tapered toward the outer periphery of the fin whereby on rotation of the rigid cylinder and the plastic sleeve secured thereto the integral, helical auger fin will be rotated, a rigid trough closely surrounding a portion of the rigid cylinder, plastic sleeve and helical auger fin over approximately 180 degrees of the helical auger fin, and means for rotating the cylinder, plastic sleeve and helical auger fin connected to the rigid cylinder whereby granular material positioned in the trough will be moved along the trough on rotation of the cylinder, sleeve and helical auger fin.

* * * * *